US00PP10196P

United States Patent [19]

Wain

[11] Patent Number: Plant 10,196

[45] Date of Patent: Jan. 13, 1998

[54] CHRYSANTHEMUM PLANT NAMED 'PUFFIN'

[75] Inventor: Peter Wain, Portsmouth, United Kingdom

[73] Assignee: Cleangro Limited, Chichester, United Kingdom

[21] Appl. No.: 751,847

[22] Filed: Nov. 18, 1996

[51] Int. Cl.[6] ..... A01H 5/00

[52] U.S. Cl. ..... Plt./82.4

[58] Field of Search ..... Plt./74.1, 82.4

*Primary Examiner*—Howard J. Locker

*Attorney, Agent, or Firm*—C. A. Whealy

[57] ABSTRACT

A distinct cultivar of Chrysanthemum plant named 'Puffin', characterized by its tall, vigorous and rapid growth rate; large daisy-type inflorescences; light pink ray florets with bright greenish yellow disc florets; numerous inflorescences per plant; numerous disc florets per inflorescence; long and strong peduncles; and good garden performance.

2 Drawing Sheets

The present invention relates to a new and distinct cultivar of garden Chrysanthemum plant, botanically known as *Dendranthema grandiflora* and referred to by the cultivar name Puffin.

The new cultivar is a product of a planned breeding program conducted by the inventor in Chichester, West Sussex, United Kingdom. The objective of the breeding program was to create new garden Chrysanthemum cultivars having desirable inflorescence colors and good garden performance.

The new cultivar originated from a cross made by the inventor of the commercial cultivar Stargazer (U.S. Plant Pat. No. 5,695) as the female, or seed, parent with the proprietary selection 10/GM/94 as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Puffin'. These characteristics in combination distinguish 'Puffin' as a new and distinct cultivar:

1. Tall, vigorous and rapid growth rate.
2. Large daisy-type inflorescences.
3. Light pink ray florets with bright greenish yellow disc florets.
4. Numerous inflorescences per plant.
5. Numerous disc florets per inflorescence.
6. Long and strong peduncles.
7. Good garden performance.

The cultivar Puffin has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum are more upright and vigorous, have larger inflorescences, retain ray floret color longer and flower later than plants of the female parent, the cultivar Stargazer. In addition, plants of the new Chrysanthemum have ray florets that are lighter in color than ray florets of plants of the cultivar Stargazer. In the same comparisons, plants of the new Chrysanthemum are taller, more open in plant habit, more vigorous, have larger inflorescences and flower earlier than plants of the male parent, the proprietary selection 10/GM/94. In addition, plants of the new Chrysanthemum have light pink ray florets whereas plants of the proprietary selection 10/GM/94 have yellow ray florets.

Plants of the new Chrysanthemum can be compared to the cultivar Naomi (U.S. Plant Pat. No. 7,513). However, in side-by-side comparisons conducted in Oxnard, Calif. under commercial practice, plants of the new Chrysanthemum differed from plants of the cultivar Naomi in the following characteristics:

1. Plants of the new Chrysanthemum are taller and more vigorous than plants of the cultivar Naomi.
2. Plants of the new Chrysanthemum have more leaves per lateral stem and longer petioles than plants of the cultivar Naomi.
3. Plants of the new Chrysanthemum flower later than plants of the cultivar Naomi.
4. Plants of the new Chrysanthemum have larger inflorescences than plants of the cultivar Naomi.
5. Ray florets of plants of the new Chrysanthemum are light pink in color and ray florets of plants of the cultivar Naomi are lavender in color.
6. Plants of the new Chrysanthemum have more disc florets and a larger disc diameter than plants of the cultivar Naomi.
7. Plants of the new Chrysanthemum have considerably longer and stronger peduncles than plants of the cultivar Naomi.

A detailed comparison of plants of the new Chrysanthemum and the cultivar Naomi appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Puffin' with one cutting in the container.

The second photograph comprises a close-up view of five leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, California, under commercial practice in a glass-covered greenhouse with average night temperatures of 18° C., average day temperatures of 30° C., and light levels of 2,000 (cloudy conditions) to 9,000 (sunny conditions) footcandles.

After sticking unrooted cuttings of the new cultivar, plants ceived 4 weeks of long day/short nights followed by short ıy/long nights until flowering. Measurements and numeri- ıl values represent ranges or averages for six typical ɔwering plants.

ɔtanical classification: *Dendranathema grandiflora* culti- var Puffin.

ɔmmercial classification: Garden chrysanthemum.

ırentage:

*Female, or seed, parent.*—*Dendranthema grandiflora* commercial cultivar Stargazer (U.S. Plant Pat. No. 5,695).

Male, or pollen, parent.—*Dendranthema grandiflora* proprietary selection 10/GM/94.

opagation:

*Type.*—Terminal tip cuttings.

*Time to rooting.*—10 to 12 days with soil temperatures of 20° C.

*Rooting habit.*—Fine, fibrous and well-branched.

ant description:

*Appearance.*—Perennial herbaceous garden plant. Tall and vigorous with a rapid growth rate, stems upright.

*Plant height.*—About 26 cm.

*Lateral branch length.*—About 24 cm.

*Quantity of lateral branches after removal of apical meristem.*—About 3.

*Stem color.*—139B.

*Foliage description.*—Number of leaves per plant: About 57. Number of leaves per lateral branch: About 19. Leaf arrangement: Alternate. Leaf size, fully expanded: Length: About 5.3 cm. Width: About 4.8 cm. Leaf apex: Rounded apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 2.9 cm. Color: Young foliage adaxial surface: 137A. Young foliage abaxial surface: 137C. Fully expanded foliage adaxial surface: 137A. Fully expanded foliage abaxial surface: 137C. Venation abaxial surface: 137D. Venation adaxial surface: 137C. Petiole: 137D.

lorescence description:

*Appearance.*—Daisy-type inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 54 days later.

*Quantity of Inflorescences.*—About 7 inflorescences per flowering stem.

*Inflorescence size.*—Diameter: About 5.2 cm. Depth (height): About 1.1 cm. Diameter of disc: About 1.3 cm.

*Opening inflorescences.*—Bud shape: Spherical, flattened. Bud size: Length: About 9 mm. Width: About 1.3 cm. Bud color: 62D.

*Ray florets.*—Shape: Spatulate, broad spoon with tubular base. Size: Length: About 2.4 cm. Width: About 6 mm. Apex: Narrow tri-dentate. Base: Acute, tubular. Margin: Entire. Texture: Smooth, matte and glabrous. Aspect: Flat. Number of ray florets per inflorescence: About 60. Color: When opening, adaxial surface: 62C. When opening, abaxial surface: 62D. Mature, adaxial surface: 65C. Mature, abaxial surface: 62D. Fading to: 65D.

*Disc florets.*—Shape: Tubular. Size: Length: About 4 mm. Width: About 1 mm. Number of disc florets per inflorescence: About 150. Color: Immature: 154D. Mature: 154C.

*Peduncle.*—Aspect: Strong and angled 35 to 45° to the stem. Length: First peduncle: About 8.8 cm. Fourth peduncle: About 11.2 cm. Texture: Pubescent. Color: 147C.

*Reproductive organs.*—Androecium: Present on disc florets only. Anther color: 12A. Pollen: Small amount of pollen, 12A in color. Gynoecium: Present on both ray and disc florets. Style color: 154C.

Disease resistance: No known Chrysanthemum diseases observed to date on plants grown under commercial greenhouse conditions.

Seed production: Seed production has not been observed.

CHART A

| CHARACTERISTIC | 'PUFFIN' | 'NAOMI' |
|---|---|---|
| GROWTH HABIT | Tall | Medium |
| PLANT HEIGHT | About 26 cm | About 22 cm |
| LATERAL BRANCH LENGTH | About 24 cm | About 19 cm |
| GROWTH RATE | Rapid | Moderate |
| VIGOR | High | Moderate |
| STEM COLOR | 139B | 146D |
| QUANTITY OF LEAVES PER LATERAL BRANCH | About 19 | About 14 |
| PETIOLE LENGTH | About 2.9 cm | About 2 cm |
| YOUNG FOLIAGE COLOR, ADAXIAL SURFACE | 137A | 147A |
| YOUNG FOLIAGE COLOR, ABAXIAL SURFACE | 137C | 147B |
| MATURE FOLIAGE COLOR, ADAXIAL SURFACE | 137A | 147A |
| MATURE FOLIAGE COLOR, ABAXIAL SURFACE | 137C | 147B |
| PETIOLE COLOR | 137D | 147C |
| TIME TO FLOWER | About 54 days | About 49 days |
| INFLORESCENCE DIAMETER | About 5.2 cm | About 4.8 cm |
| BUD COLOR | 62D | 75B |
| RAY FLORET APPEARANCE/ASPECT | Broad spoon with tubular base, flat | Narrow, long-handled spoon, slightly cupped |
| RAY FLORET APEX | Narrow tri-dentate | Emarginate |
| RAY FLORET COLOR, WHEN OPENING, ADAXIAL | 62C | 80C |
| RAY FLORET COLOR, WHEN OPENING, ABAXIAL | 62D | 75C |
| RAY FLORET COLOR, MATURE, ADAXIAL | 65C | 75A |
| RAY FLORET COLOR, MATURE, ABAXIAL | 62D | 75D |
| RAY FLORET COLOR FADING TO | 65D | 75C |
| QUANTITY OF DISC FLORETS PER INFLORESCENCE | About 150 | About 118 |
| DIAMETER OF DISC | About 1.3 cm | About 1.1 cm |
| PEDUNCLE LENGTH, FIRST | About 8.8 cm | About 1.5 cm |
| PEDUNCLE LENGTH, FOURTH | About 11.2 cm | About 3.5 cm |
| PEDUNCLE STRENGTH | Strong | Moderate |
| PEDUNCLE ANGLE TO STEM | 35 to 45° | 20 to 25° |
| ANTHER COLOR | 12A | 17A |
| POLLEN COLOR/AMOUNT | 12A, little | 17A, abundant |

It is claimed:

1. A new and distinct cultivar of Chrysanthemum plant named 'Puffin', as illustrated and described.

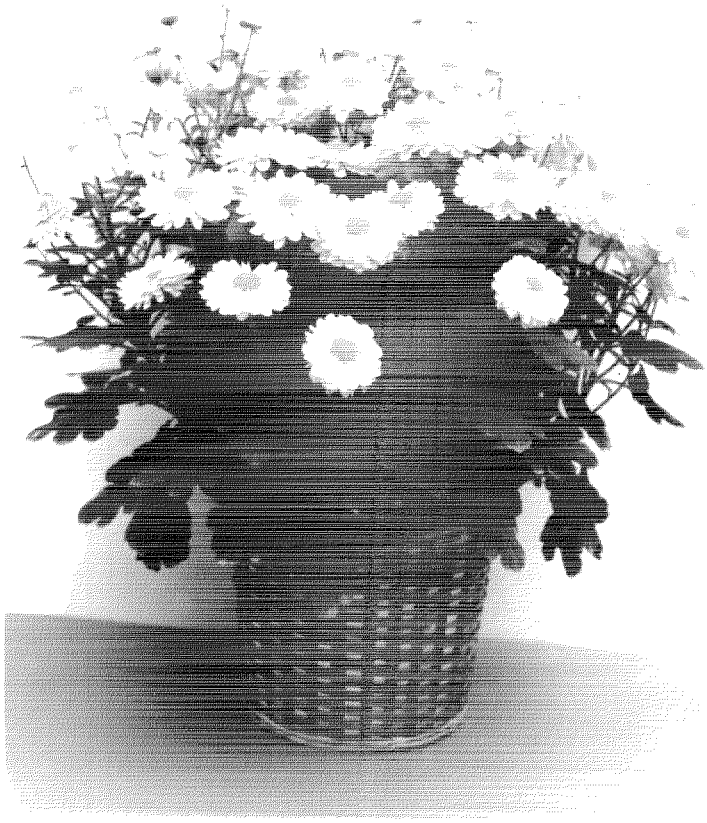

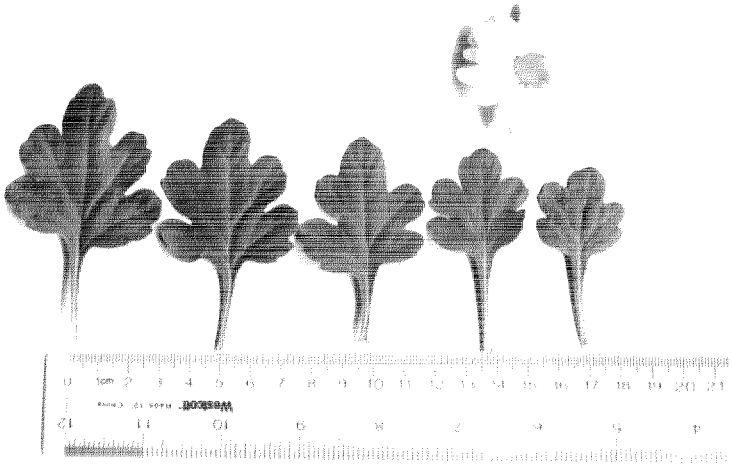

* * * * *